United States Patent [19]
Sheehan et al.

[11] Patent Number: 5,826,582
[45] Date of Patent: Oct. 27, 1998

[54] EAR PHONE ASSEMBLY FOR USE WITH A HEARING SCREENER

[75] Inventors: Neil J. Sheehan, Palo Alto; Robert T. Stone, Sunnyvale, both of Calif.

[73] Assignee: Natus Medical Inc., San Carlos, Calif.

[21] Appl. No.: 861,724

[22] Filed: May 22, 1997

[51] Int. Cl.[6] .................................................. A61F 11/00
[52] U.S. Cl. ........................................ 128/864; 128/866
[58] Field of Search .................................. 128/857, 858, 128/864–868; 381/71, 72; 2/209, 423, 455

[56] References Cited

U.S. PATENT DOCUMENTS

| | | | |
|---|---|---|---|
| 3,938,614 | 2/1976 | Ahs | 181/129 |
| 3,944,018 | 3/1976 | Satory | 181/33 |
| 4,009,707 | 3/1977 | Ward | 128/2 |
| 4,024,499 | 5/1977 | Bosscher | 340/16.2 |
| 4,036,235 | 7/1977 | Hathaway | 128/292 |
| 4,134,153 | 1/1979 | Voorhees | 2/174 |
| 4,344,425 | 8/1982 | Strauss | 128/152 |
| 4,375,744 | 3/1983 | Briner et al. | 57/96 |
| 4,408,605 | 10/1983 | Doerr | 128/864 |
| 4,437,538 | 3/1984 | Ohlsson | 181/129 |
| 5,134,659 | 7/1992 | Moseley | 381/72 |
| 5,138,663 | 8/1992 | Moseley | 381/71 |
| 5,704,069 | 1/1998 | Andersson | 128/864 |
| 5,749,099 | 5/1998 | Voorhees | 128/866 |

*Primary Examiner*—Michael A. Brown
*Attorney, Agent, or Firm*—Orrick, Herrington & Sutcliffe

[57] ABSTRACT

An ear phone assembly is provided for use with a hearing screening instrument to test infants for hearing impairments. The ear phone includes a generally D-shaped reusable cover including a back wall having a perimeter, a side wall extending from the perimeter to define a cavity for receiving an infant's ear, a port in the cover to receive and support a transducer, and a generally D-shaped disposable element that is adhesive coated on two sides to be secured to the cover and to the patient's head. The cover may have a notch located along the perimeter of the re-usable body for removing the disposable element. A liner is used to cover the disposable element adhesive sides to protect them from contamination during packaging and prior to use. The disposable element may have a die cut so that a portion of it can be removed to make the ear phone adjustable for infants with large ears. The ear phone is low in cost and capable of being used with any conventional hearing screening equipment.

36 Claims, 3 Drawing Sheets

5,826,582

EAR PHONE ASSEMBLY FOR USE WITH A HEARING SCREENER

FIELD OF THE INVENTION

The present invention generally relates to ear phones which cover the ear, and more particularly to ear phones for infants for use in hearing screening tests.

BACKGROUND OF THE INVENTION

It is known to conduct tests to identify hearing impairments in humans (also known as "hearing screening"). It is critical and advantageous to determine whether or not any hearing impairments exist at an early age, such as in newborns and infants. This is because the earlier a problem is diagnosed and therapy undertaken, the more likely the therapy or other intervention will minimize the potential problems and costs associated with the identified hearing impairments or loss.

Over the years, hearing screening techniques have been developed which inject a sound input into the ear and detect a response to that input. The response is related to the characteristics of the sound input and the conditions inside the ear, the neural connections, and the vibration transmission mechanism of the ear. The response can be analyzed to assess the hearing of the patient.

In many cases, and in particular in the case of infants, hearing screening is performed by using an ear phone having a cavity that fits closely about the ear. Auditory tones or "clicks" are fed into the ear phone cavity, and the response generated by the patient's ear and the neural conduction system in response to the auditory tones is sensed by a transducer. The transducer may be, for example, a microphone, suitable electrodes, piezo electric materials and like devices that generate signals representative of the response to the auditory input. These signals are then processed and the result (as well as the detected signals, if desired) can be displayed on a monitor or other viewing device for analysis of the patient's hearing.

A common problem using this method is that ambient noises, internal or external to the cavity, are capable of interfering with the stimulus or the response signals, and, thus, the result. In most cases, the monitoring equipment has mechanisms, such as microphones, for detecting and compensating for ambient background noise. However, compensating for noise inside the cavity is difficult.

U.S. Pat. No. 4,930,520 to Liverani provides a disposable ear phone for testing the hearing in infants which includes a toroidal baffle of anechoic, insulative foam, a clear planar window plastic sheet adhered to one side of the baffle defining a cavity, and an adhesive coating on the other side of the baffle for bonding the disposable ear phone to the region surrounding the infant's ear. The ear phone is capable of being used with transducers for transferring acoustical energy through a pneumatic tube to the infant's ear for testing. The Liverani device has been commercialized and is sold under the trademark EAR COUPLERS® disposable earphones by Natus Medical Incorporated, the assignee of this invention.

One of the problems with the Liverani device is that the ear phone is somewhat cost-ineffective in that the entire ear phone is not re-usable and must be disposed of after each use, and one device is used per ear. In particular, the construction and use of the device requires, according to accepted general medical practices, that after use it be disposed of as medical waste. Another problem of the Liverani ear phone is that its construction is not capable of adjustment for infants with different size ears. As a result, it is necessary to manufacture different size ear phones and maintain an inventory of the different sizes to obtain acceptable test performance for patients having different sized ears.

Thus, there remains a need for an improved ear phone that overcomes the problems of the known device and, further, provides advances that improves the attenuation of ambient and external noise inside the cavity of the ear phone.

OBJECTS AND SUMMARY OF THE INVENTION

Accordingly, it is an object of the present invention to provide an ear phone, particularly for screening the hearing of infants, which has an improved cost effectiveness in that it comprises a durable, reusable cover and a low-cost, smaller disposable element that is easily attached to the durable part for use and easily removed therefrom after use.

It is another object to provide a disposable element that is capable of being used with ears of different sizes.

It is another object of the invention to provide an ear phone that is generally free from external noise.

It is yet another object of the invention to provide a disposable element that is interchangeable in that it can be used with either a left ear cover or a right ear cover for use with testing of the left ear or the right ear.

Broadly, the present invention is directed to an ear phone assembly, which is useful for measuring auditory signals in infants, including a durable cover and a disposable element. The disposable element has a thickness and an adhesive on each side of the thickness such that one side of the disposable element becomes adhered to the cover and the other side is pressed in contact with the patient's skin around the ear. Thus assembled, the ear phone assembly is secured to the patient's head about the ear, and forms a chamber which acoustically isolates the ear from the ambient environment.

In a preferred embodiment, the cover includes a port through which a transducer is inserted to conduct hearing screening tests. This permits the use of a highly durable transducer, which may be more durable than the cover and needs only to be cleaned after use.

After the hearing screening tests are completed, the ear phone assembly can be removed from the patient, the disposable element separated from the cover and disposed of, the transducer removed from the port, and the reusable durable cover can be cleaned and/or sterilized for the next use.

The disposable elements are pre-formed with a toroidal shape corresponding to the perimeter of the cover, and the adhesives are pre-coated on the disposable element sides and, prior to use, are protectively covered with removable liners.

In a preferred embodiment, the cover comprises a cavity and a flange to which the disposable element is adhered. The cavity provides a generally flat surface which extends over the ear when the ear phone assembly is in place. The cover may, however, be contoured so as to conform generally to the shape of the patient's head about the ear. As is well known, the area around the ear is not flat. Rather, the area is curved in three dimensions. The cover and in particular, the flange, may thus be provided with a shape that conforms to such a surface. For example, the cover may be formed in a manner that can be described as having a relatively flat body with a folded edge. More specifically, the cover is "bent" along a diagonal such that the bend is actually provided with a radius so the cover conforms well to the head. More preferably, left ear covers and right ear covers are separately provided having the appropriate bends to to obtain a better fit for the patient.

The port, which receives the transducer, is preferably an integral part of the cover. Further, the port also may include a projecting structure for supporting or at least engaging a transducer in a non-rotating relationship.

Further, as applicants have discovered, an improved cover is obtained by providing the cover, and the corresponding disposable element, with a generally D-shape, such that the straight side of the "D" is flat and corresponds generally to a vertical axis, and the curved portion of "D" is basically symmetrical about a horizontal axis midpoint between the ends of the vertical axis. In this embodiment, the cover is "bent" about a diagonal extending from a sharp corner of the D-shape to the catty-corner rounded corner of the "D". This bent structure advantageously provides for using the smaller cavity size of the D-shape, as compared to the larger cavity size of the Liverani device which is generally symmetrical about its vertical axis, and a better fit against the patient's head. This facilitates a generally noise-free chamber closely fitting about the ear in an improved air tight relationship for hearing screening.

BRIEF DESCRIPTION OF THE DRAWINGS

Further features of the invention, its nature, and various advantages will become more apparent from the accompanying drawings, and the following detailed description of the invention, in which like reference numerals refer to like elements, and in which.

DETAILED DESCRIPTION OF THE DRAWINGS

Figure 1:
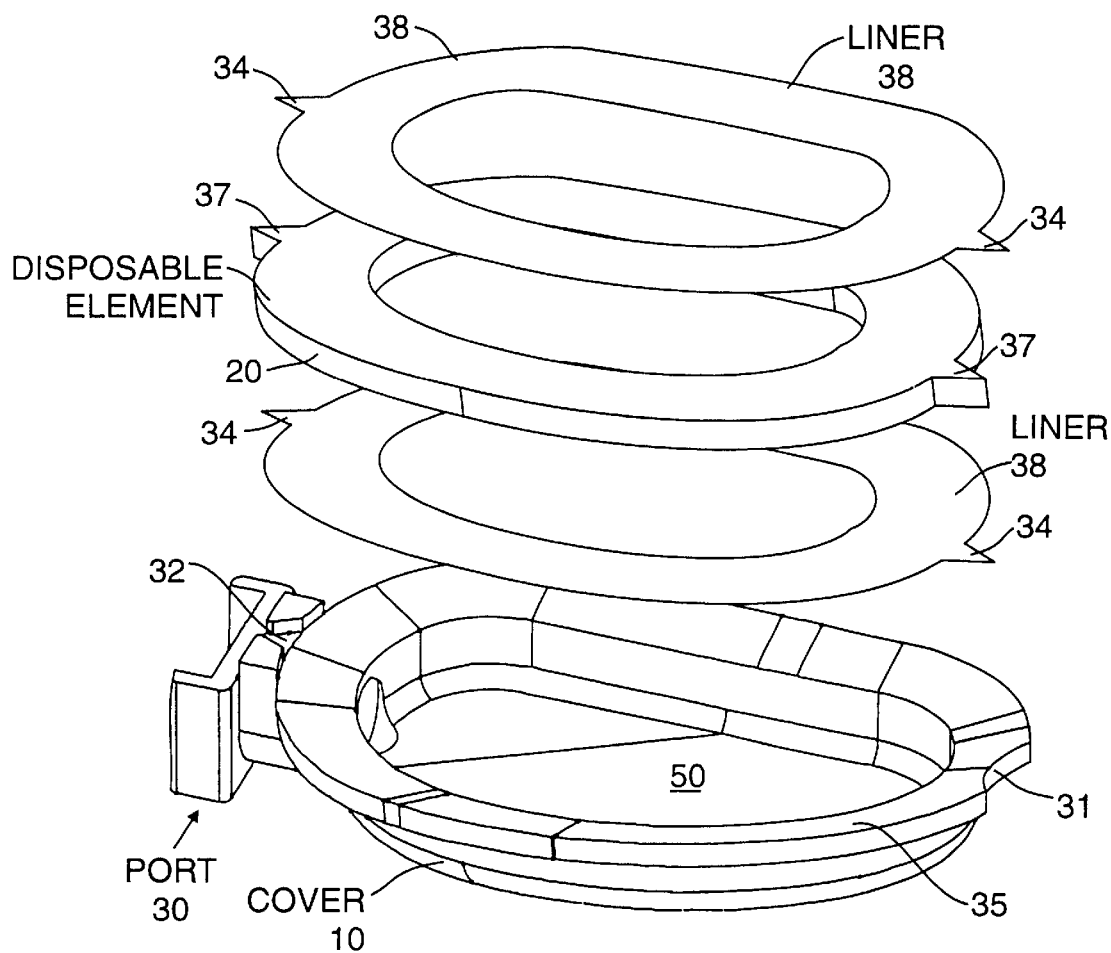
FIG. 1 is an exploded elevated perspective view of an ear phone assembly for a left ear in accordance with a preferred embodiment of the present invention.

Referring to FIG. 1, the left ear phone assembly 3 of the present invention comprises a cover 10 and a disposable element 20. The cover 10 is a durable, reusable element that includes a cavity 50 to cover the ear without interfering with the normal shape of the ear. The disposable element 20 is a generally planar element that is to be mounted to the cover 10 on one side and to the patient's head on the other side. The disposable element 20 thus effectively increases the depth of cavity 50 which covers and receives the patient's ear. Although not shown, the cover for a right ear phone in accordance with the present invention is the mirror image of the left ear phone assembly cover shown.

With reference to FIGS. 1–8, cover 10 includes a proximal end 6 and a distal end 8 and is shown having generally a D-shape. It should be noted, however, that cover 10 can have any shape, e.g., circular, oval, trapezoidal, etc., as well as asymmetrical shapes such as the D-shape, that will permit the patient's ear to be adequately covered during use. Cover 10 includes a back wall 19 having a perimeter that joins to a side wall 13 to define cavity 50. Cover 10 also includes a flange 35 that is connected to side wall 13 and extends around the perimeter, and a notch 31 in the flange 35.

In one embodiment, flange 35 is generally inwardly sloped, to provide better conformity to and a better fit against the patient's head around the ear, as shown in FIGS. 2 and 5–8. The flange 35 may extend outwardly from the side wall 13. Alternatively, the flange may straddle side wall 13.

Notch 31 is positioned along the perimeter 23 of the flange 35 to provide easy removal of the disposable element 20 from the cover, as will be described below. Notch 31 may, for example, be positioned at distal end 8 (shown in FIG. 2) or midway between distal end 8 and proximal end 6 (not shown) or elsewhere in flange 35. In one embodiment, the notch 31 is preferably finger-tip shaped having a radius. However, the notch may be any convenient shape, for example, wedge, oval or rectangular, for allowing the user to grasp the previously attached disposable element 20.

It should be understood that, in an alternate embodiment, if the thickness of the side wall 13 is sufficiently large, flange 35 may be omitted.

Cover 10 is preferably made of a substantially rigid material having an acoustical impedance that is higher than that of external air. As a result, external acoustical sounds are deflected off of cover 10, leaving the cavity 50 sufficiently and generally free of ambient and external noise for hearing screening. Suitable materials include rubber, elastomers, metals and plastics.

Cover 10 may be formed by injection molding, liquid resin casting, or other methods that are well known in the art. It may be formed as a unitary piece (e.g., cast, stamped or molded) or as an assembly of pieces secured together (e.g., epoxied, glued or welded).

Preferably, at least back wall 19 is made of a generally clear material, for example, a polypropylene or a polycarbonate, to provide easy viewing to the user for the purpose of proper positioning during operation and to protect the patient's ear from ambient noises.

Advantageously, the materials used and the process of manufacturing the cover 10, as discussed above, allow cover 10 to be cleaned and/or sterilized. Depending on the material used, cover 10 may be autoclaved as in the case of a polycarbonate. Advantageously too, cover 10 can be resterilized and re-used numerous times after each hearing screening procedure, thereby improving the cost-efficiency of the ear phone assembly 3.

Figure 4:
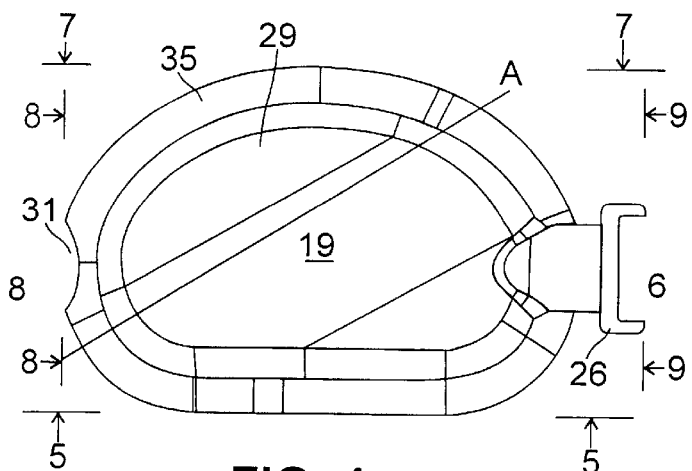
FIG. 4 is a top plan view of the cover of FIG. 2.
Figure 5:
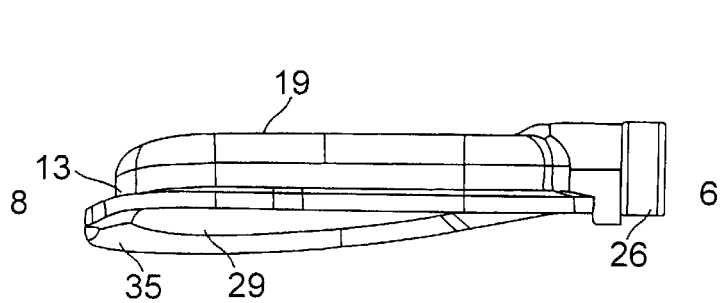
FIG. 5 is a side view taken along line 5—5 of FIG. 4.
Figure 8:
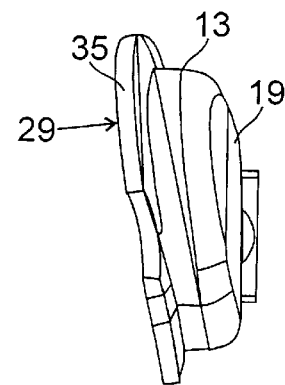
FIG. 8 is an end view taken along line 8—8 of FIG. 4.
Figure 7:
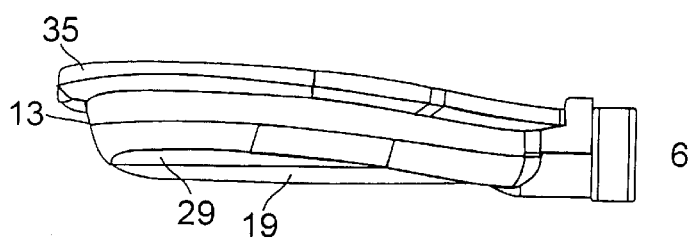
FIG. 7 is a side view taken along line 7—7 of FIG. 4.

As illustrated in FIGS. 4–8, the folded or bent portion 29 is the area to the upper left portion relative to line A of FIG. 4, and the degree of bending needed to conform the cover including the flange to the head is illustrated in the different views of the referenced drawings. The bent portion is provided with an angle of approximately ten degrees. It should be understood that the bend is a part of the cover as formed, and is not actually the result of straining the cover 10, although the latter also could occur.

Referring to FIGS. 2–7, port 30 includes a mass of material having an aperture 39 extending therethrough which opens into side wall 13, a U-shaped projection 26, and two beveled projections 32A defining therebetween a receptacle or groove 32. Groove 32 is used to position correctly the disposable element 20 in superposition on flange 35, as will be described. It should be understood that groove 32 need not be a part of port 30, but could be located anywhere on or near flange 35 where it can be conveniently used.

In operation, port 30 receives a transducer (not shown) a portion of which passes through aperture 39 into cavity 50. Transducer 50 may have a ribbed cylinder to provide an air-tight friction-fit to the inside of aperture 39. In this regard, aperture 39 is preferably circular in cross-section and cylindrical. A suitable transducer is the product known as the Acoustic Transducer Assembly, part no. 040176, available from Natus Medical Incorporated, San Carlos, Calif., the assignee hereof, and sold for use with the models ALGO 1E™ and ALGO 2™ hearing screening instruments, also available from Natus Medical. It should be understood that aperture 39 may have any shape that will couple securely, tightly, and removably to a transducer. Although the transducer forms no part of the present invention, it is contemplated that the length of the aperture 39 be longer than the portion of the transducer that is inserted into aperture 39. This, advantageously, minimizes the likelihood of contact between the transducer and the patient's ear, in particular the pinna.

The U-shaped projection 26 is proximate to aperture 39 and projects from port 30 to engage the transducer and minimize the rotation of the transducer in use, e.g., as a result of patient movement. It should be understood that in place of the U-shaped projection 26, a flange, a plurality of flanges, or a pin and hole assembly, or some other well-known device for engaging a transducer to minimize rotation relative to cover 10, may be used.

Figure 9:
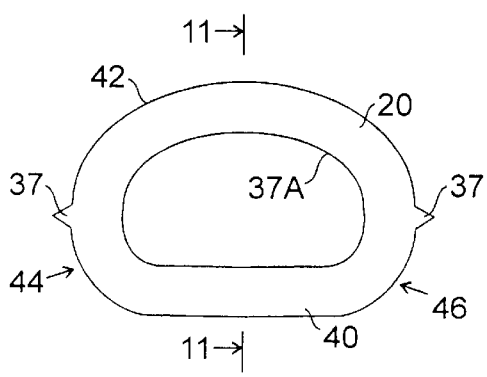
FIG. 9 is a plan view of a preferred embodiment of the disposable element of FIG. 1.
Figure 10:
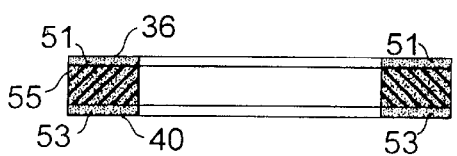
FIG. 10 is a sectional view taken along lines 11—11 of FIG. 9.

Referring to FIGS. 1 and 9–10, disposable element 20 has an toroidal or annular structure having a first side 36 and a second side 40, an external perimeter 42 and an interior perimeter 37A. Each perimeter is preferably D-shaped. However, the disposable element 20 may be any shape that on the one hand allows the patient's ear to pass through the interior perimeter 37A, and on the other hand secures to flange 35 of cover 10 for securing the ear phone assembly 3 to the patient.

Preferably, disposable element 20 also has V-shaped projections 37 at its top and bottom, which are used in aligning the disposable element 20 to the cover 10 in the proper orientation, as will be discussed. Indeed, projections 37 define the orientation of disposable element 20 relative to a reference point, such as groove 32, for superposition on flange 35 in the proper relationship.

In a preferred embodiment, each of the first and second sides 36 and 40 comprise an adhesive surface 51 and 53 respectively (see FIG. 10). The adhesive may be coated on or impregnated into a support material 55, or the support material 55 can be covered with a double sided adhesive tape. The adhesive is used to secure one side of disposable element 20 to flange 35. The other side of disposable element 20 is secured by the adhesive to the head. Preferably, disposable element 20 has substantially the same shape as flange 35 such that disposable element 20 covers flange 35 entirely. In one embodiment, disposable element 20 may overlap all of flange 35 and extend inwardly beyond the dimensions of flange 35. One of the V-shaped projections 37 preferably extends over notch 31 at one end in an exposed manner and another of projections 37 engages groove 32 at the other end. The exposed projection 37 additionally facilitates removal of the disposable element 20 from cover 10 by peeling it off.

The adhesives used in disposable element 20 are preferably pressure sensitive and approved for medical applications, as are well-known in the art. The adhesive is selected to have at least enough strength to stick to the patient's head, creating an air-tight seal, for hearing screening, yet be weak enough for easy removal of disposable element 20 from engagement with the patient's head without trauma to the patient. In addition, the adhesive should be strong enough to create an air-tight seal between the disposable element 20 and the cover 10, and allow easy removal of the disposable element from the cover. Suitable adhesives include a hydrogel, such as adhesive product #63B distributed by Promeon, and acrylic (acrylate), for example, double coated medical tapes and transfer adhesives such as product numbers 1522, 9874, 1524, and 9879, each of which is available from 3M Health Care, St. Paul, Minn. These tapes may be transparent polyethylene coated films or polyester fiber based tapes which are generally sold with one side covered by a silicone treated Kraft-Glassine paper liner. The adhesive thus may be affixed to two sides of a sheet of support material 55 with the liner intact to construct an adhesive coated support material. The disposable elements 20 are then formed from such adhesive coated sheets, as discussed further below.

In one embodiment, the disposable element 20 is symmetrically constructed about a horizontal axis and fully interchangeable. By this it is meant that disposable element 20 may be selectively used for the right ear or the left ear, and can be positioned on cover 10 without having to differentiate between which adhesive covered side (36 or 40) contacts flange 35, or which of the ends 44 and 46 is to be at the proximal end 6 of cover 10. In this case, the sides 36 and 40, and the ends 44 and 46 are mirror images of each other with effectively the same type, quality, and adhesion strength characteristics on each side. Thus, either side can be adhered to the cover 10 (or the head) and a given disposable element can be used in either orientation for the left ear cover or the right ear cover.

In an alternative embodiment, a hydrogel adhesive may be used on the side that is to contact the patient's head, and an acrylic adhesive used on the side to contact cover 10. In this case, disposable element 20 is not fully interchangeable, because of the differences in the strength, quality, etc. of the different adhesives on its first and second sides, 36 and 40. In this embodiment, one side, namely the side having the hydrogel adhesive, is preferably used to contact the patient's head. This is because the hydrogel has adequate adhesion to tissue, but is easier to remove from the patient than an acrylic adhesive. Nevertheless, even in this embodiment, disposable element 20 remains interchangeable about its ends 44 and 46, due to its symmetry about the horizontal axis. Thus, the same disposable element 20 can be used for the left ear cover and the right ear cover such that the side having the acrylic adhesive is disposed to couple to the cover 10.

The interchangeability of disposable element 20 is particularly advantageous because it reduces the number of components that must be manufactured and maintained in inventory, thereby reducing the effective cost for the manufacture and to the user. Further, by using the asymmetrical D-shape, an improved cavity 50 shape is obtained for which the disposable element 20 has left and right ear interchangeability. This reflects an improvement in acoustic isolation over the larger dimensioned cavity of the prior art Liverani structure.

Disposable element 20 is preferably constructed of a support material 55 that is a resilient open-celled foam, in which air is blocked from freely moving from one side of the foam to the other due to the tortuous paths formed by the open cell structure of the foam. The air impermeability is enhanced by the adhesive coatings on the two sides. The open cell foam also is resilient and provides comfort and easy conformability to the patient's head. Hence, in a preferred embodiment, the disposable element 20 is a toroidal foam cushion. The opened-cell foam may be any that is conventional in the art, for example, polyvinylchloride (PVC) foam.

A closed-cell foam may also be employed as support material 55, whereby air cannot pass through the foam. A suitable closed-cell foam may be polyethylene foam.

Thus, by the use of a foamed support material 55, the amount of ambient noise capable of passing through the disposable element 20 is minimized.

With reference to FIG. 1, two liners 38 are illustrated, each as having a pair of tabs 34 at opposite ends, corresponding to the pair of projections 37 of the disposable element 20. Each liner 38, however, may have any number of tabs, e.g, one or more than two. Each liner 38 is preferably D-shaped to match the shape of the side of disposable element 20, however, it may have any shape that covers the adhesive surface 51 or 53 of disposable element 20.

In packaging, that is prior to use, a first liner 38 covers one of the adhesive covered sides of disposable element 20 and a second liner 38 covers the other side of disposable element 20. Liners 38 are provided to keep disposable element 20 sufficiently free of contamination prior to use. Liner 38 also lessens the possibility of the adhesive losing its tackiness or strength. Liners 38 are easily removed from sides 36 and 40 by pressing inwardly on disposable element 20 at projections 37, thereby causing tabs 34 to separate from the underlying adhesives of disposable element 20. Alternatively, the user may pull off each liner 38 by pulling back on its tab 34. The liner may be a non-woven fabric, such as Tyvek, mylar, or a release paper of the kind well known in the art, such as Kraft-Glassine paper, which paper is preferably silicone treated. Liner 38 is preferably a release paper because it is inexpensive and may be disposed of easily. Preferably, the first and second liners 38 are identical in structure and are the liners commercially provided with the double sided adhesive tape or transfer adhesive applied to the two sides of support material 55. Liner 38 may also be a split liner whereby the liner is cut along a line into two separate liners such as a "crack and peel" liner.

Figure 2:
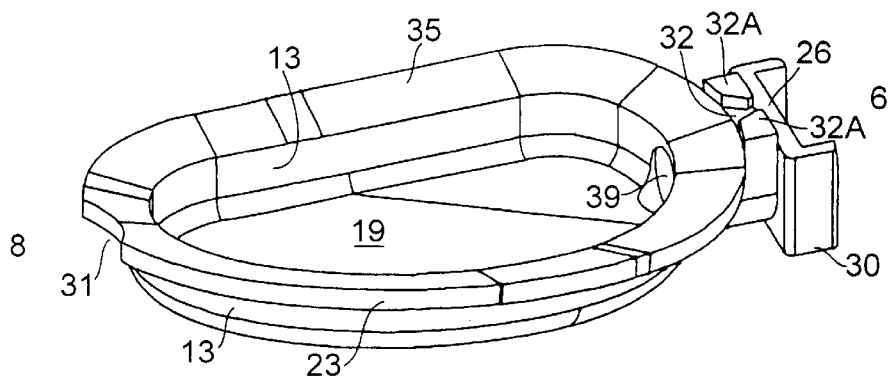
FIG. 2 is a bottom elevated perspective view of a right ear cover which can be seen to be a mirror image of the left ear cover of FIG. 1.
Figure 3:
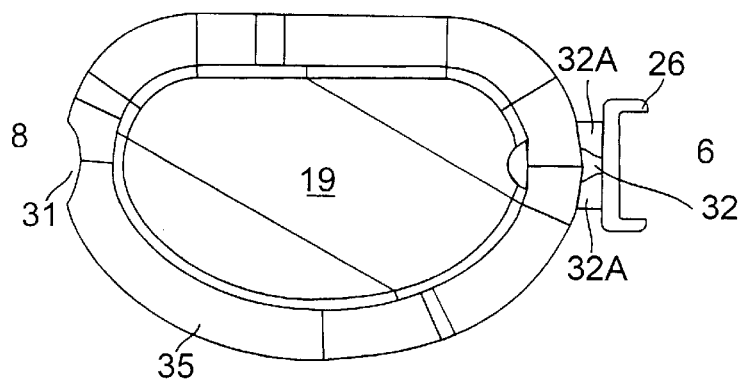
FIG. 3 is a bottom plan view of the cover of FIG. 2.
Figure 6:
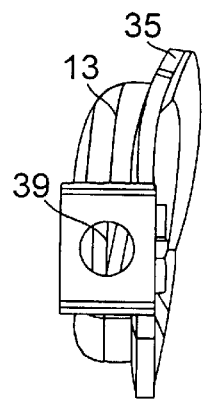
FIG. 6 is an end view taken along line 9—9 of FIG. 4.

Referring to FIGS. 2, 3, and 4, groove 32 of port 30 is designed to receive one of the projections 37 of disposable element 20, preferably after removal of the liner 38 over the side to be pressed against flange 35. This is to provide easy alignment of disposable element 20 with flange 35. Projections 37 are slightly smaller than groove 32 such that the projections 37 may be easily inserted and removed during alignment. Groove 32 and projections 37 may be of any shape, preferably complementary (that is, male and female mating) shapes. In a preferred embodiment, the groove 32 and projections 37 are both generally V-shaped, respectively the female and male V-shapes.

Disposable element 20 is formed by coating both sides of a support material 55, e.g., a sheet of foam, with adhesive and covering the adhesive coated sides with a liner paper, either during or after the coating process. The lined foam sheet is then processed to obtain the disposable element. For example, disposable element 20 is generally constructed using a flat bed or "cookie sheet" technique whereby disposable element 20 is die-cut from the lined foam sheet of material, by a cutter that outlines the general shape of the disposable element. This is a technique that is conventional in the art. For manufacturing, the disposable element 20 is made thin, for example, from $\frac{1}{16}$" to $\frac{1}{2}$", and preferably $\frac{1}{4}$", thick. Advantageously, this allows the use of fast-rotary die cutting which is faster and more economical that the slower conventional flatbed or "clicker press" techniques.

Figure 11:
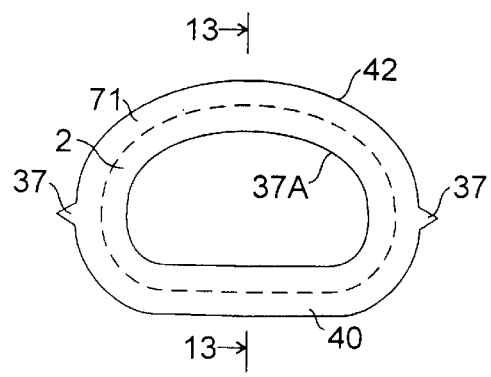
FIG. 11 is a top view of the disposable element of FIG. 1 in accordance with another embodiment of the present invention.
Figure 12:
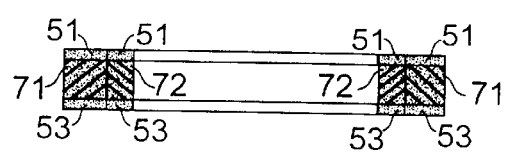
FIG. 12 is a sectional view taken along lines 13—13 of FIG. 11.

In addition, a "double" die-cut design may be used, as shown in FIGS. 11 and 12, to provide the disposable element with two nested planar annular sheets 71 and 72. Annular sheet 71 is outward of annular sheet 72 such that the interior opening in disposable element 20 defined by sheet 71 (if exposed) is larger than the interior opening defined by the sheet 72. Sheet 72 is removable such that sheet 71 remains in place, thereby allowing to adjust the ear phone assembly 3 for larger size ears. Multiple die-cuts providing for multiple sheets and multiple size openings may also be used. Advantageously, use of one or more die-cut(s) in disposable element 20 minimizes the need to maintain inventory of different size disposable elements 20 for different size ears and increases manufacturing efficiency. It is noted that the die cuts may cut cleanly through the disposable element 20, or alternately may perforate the sheet, so that there is some minor tearing of the foam when annular sheets 71 and 72 are separated.

In operation, the ear phone assembly 3 is assembled as follows. The liner 37 from one of the sides of disposable element 20 is removed, thus exposing the adhesive on one side of the disposable element 20. The reusable durable cover 10 is obtained clean and/or sterile. Disposable element 20 is secured to flange 35 of cover 10, by aligning groove 32 with a projection 37 of disposable element 20, and pressing the adhesive against the flange 35. Once positioned, the remaining liner is removed from the disposable element 20, thereby exposing the side of the disposable element for engaging the patient's head. A transducer (not shown) is then (or initially) inserted into aperture 39. The cover 10 and the disposable element 20 are then placed around patient's ear, such that the mastoid is covered by the bent area 29. The disposable element 20 and cover 10, in combination, are pressed against the patient's head, forming an ambient noise blocking cavity 50 surrounding the ear, thereby allowing the transducer to couple sufficiently free of external noise.

Further, port 30 may be located in a location that is different from what is illustrated in the drawings, for example, in back wall 19. Alternatively, the port could be located in disposable element 20 to open directly into cavity 50, such that the transducer portion inserted into disposable element 20 provides a good seal to minimize any ambient noise entering the cavity 50.

It will be appreciated that the present invention may be used with conventional hearing screening equipment as is well-known in the art. For example, the models ALGO 1E™ and ALGO 2™ hearing screening machines available from Natus Medical, as well as otacoustic emission based machines.

The present invention has several advantages over the prior art including that it is easily manufactured, cost-effective whereby the cover is reusable and less disposable material is used as compared to prior devices, and allows for adjustment of the ear phone assembly for different ear sizes. Moreover, the ear phone of the present invention is simple, lightweight, and safe for use with infants.

The present invention has been described in terms of the preferred embodiments of the invention, which are presented for purposes of illustration and not of limitation. It will be appreciated that modifications, variations, and features within the scope of the invention, given the benefit of the disclosure, will occur to one of ordinary skill in the art.

We claim:

1. An ear phone assembly for use with a transducer for hearing screening comprising:
    a reusable cover having a first end, a second end and a cavity;

a disposable element having a first side and a first adhesive on the first side to secure releasably the disposable element first side to the reusable cover; and a port adapted to receive a transducer in communication with the cavity.

2. The assembly of claim 1 wherein the reusable cover is generally D-shaped.

3. The assembly of claim 2 wherein the reusable cover further comprises:

a back wall having a first perimeter, the back wall further comprising a bent portion;

a flange having a notch, a second perimeter, and a first surface, the first surface being adapted to receive the first side of the disposable element so that the disposable element overhangs the notch; and a side wall coupling the back wall first perimeter and the flange second perimeter, wherein the side wall and the back wall further comprise a cavity.

4. The assembly of claim 3 wherein the notch further comprises a finger-tip shape.

5. The assembly of claim 3 wherein the reusable cover comprises a rigid material having an acoustical impedance higher than air.

6. The assembly of claim 5 wherein the back wall material further comprises a visibly transparent material.

7. The assembly of claim 6 wherein the back wall material further comprises a polypropylene or a polycarbonate material.

8. The assembly of claim 7 wherein the back wall is in a plane and the flange first surface is generally oriented at a solid angle relative to the plane of the back wall.

9. The assembly of claim 3 wherein the cover further comprises a first shaped projection proximate the flange and the disposable element further comprises a second shaped projection adapted to engage said first shaped projection.

10. The assembly of claim 9 wherein the first shaped projection further comprises a V-shaped receptacle and the disposable element second shaped projection further comprises a V-shaped projection.

11. The assembly of claim 1 wherein the port further comprises:

a mass of material in said cover; and a cylindrical aperture extending through said mass of material and opening at said side wall.

12. The assembly of claim 1 wherein said cover further comprises at least one projection proximate said aperture positioned to engage a transducer in a non-rotational relationship.

13. The assembly of claim 12 wherein the said at least one projection further comprises a U-shaped projection having a base and two upright legs, wherein the aperture is open to the base.

14. The assembly of claim 1 wherein the disposable element is generally D-shaped.

15. The assembly of claim 1 wherein the disposable element further comprises:

a first end and a second end;

a second side adapted to contact a patient's head; and a second adhesive on said second side.

16. The assembly of claim 15 wherein the second adhesive further comprises a double sided adhesive tape.

17. The assembly of claim 15 further comprising:

a first liner and a second liner removably mounted to said first and second sides of the disposable element respectively, wherein each liner has at least one tab usable for removing each of said liner from each of said first and second sides.

18. The assembly of claim 17 wherein the at least one tab is V-shaped.

19. The assembly of claim 17 wherein each liner further comprises a generally D-shape.

20. The assembly of claim 19 wherein each liner further comprises a release paper.

21. The assembly of claim 15 wherein the first and second ends of said disposable element are symmetrical.

22. The assembly of claim 21 wherein the first and second sides of the disposable element are symmetrical and the disposable element is fully interchangeable between a patient's right ear and left ear.

23. The assembly of claim 15 wherein the first and second adhesives comprise the same adhesive.

24. The assembly of claim 15 wherein at least one of said first and second adhesives further comprises a hydrogel.

25. The assembly of claim 15 wherein the disposable element further comprises a resilient foam material.

26. The assembly of claim 25 wherein the resilient foam material further comprises an open-celled foam.

27. The assembly of claim 26 wherein the resilient foam material further comprises a PVC foam.

28. The assembly of claim 25 wherein the resilient foam material further comprises a closed-cell foam.

29. The assembly of claim 28 wherein the resilient foam material further comprises a polyethylene foam.

30. The assembly of claim 25 wherein the disposable element has at least a first annular sheet defining a first area and a second annular sheet defining a second area, said at least first and second annular sheets being co-planar and the second annular sheet circumscribing the first annular sheet, wherein the first annular sheet is removable separately from the second annular sheet.

31. The assembly of claim 25 wherein the disposable element further comprises a thickness between said first and second sides of approximately ¼" thick.

32. A method for mounting an ear phone to a patient's head for hearing screening comprising:

(a) providing an ear phone including a re-usable cover having a first end and a second end and defining a cavity therein for receiving an ear and a port adapted to receive a transducer;

(b) providing a disposable element having a first side and a second side wherein each of the first and second sides have thereon an adhesive;

(c) securing the re-usable cover to said first side of the disposable element; and (d) securing the second side of the disposable element to the patient's head, so that the cavity receives the ear sufficiently free of ambient noise.

33. The method of claim 32 wherein step (b) further comprises providing a first liner and a second liner respectively mounted on said first side and second side of the disposable element, and removing said first liner from said first side prior to step (c), and in wherein step (c) further comprises removing said second liner from said second side.

34. The method of claim 32 wherein the port further comprises an aperture and the method further comprises frictionally inserting the transducer in the aperture.

35. The method of claim 32 wherein providing the cover further comprises providing a notch in said cover so that step (c) further comprises placing said disposable element over said notch and step (d) further comprises removing the disposable element from the patient's head.

36. The method of claim 35 wherein step (d) further comprises grasping the disposable element over said notch and peeling the disposable element from the cover.

* * * * *

UNITED STATES PATENT AND TRADEMARK OFFICE
CERTIFICATE OF CORRECTION

PATENT NO. : 5,826,582
DATED : October 27, 1998
INVENTOR(S) : M. Brown

It is certified that error appears in the above-indentified patent and that said Letters Patent is hereby corrected as shown below:

Column 1, lines 58-59, after "disposable" delete "earphones" and insert -- ear phones --;

Column 1, line 63, after "is not" delete re-usable and insert -- reusable --;

Column 2, line 49, after "are" delete "pre-formed" and insert --preformed --;

Column 2, line 52, after "are" delete "pre-coated" and insert -- precoated --;

Column 2, lines 61-62, after "cover and" insert -- , --; and after "flange" delete ",";

Column 3, line 3, after "provided" insert -- , --; and after "bends" delete "to";

Column 3, line 23, after "improved" delete "air tight" and insert -- airtight --;

Column 4, line 25, after "tip" insert -- -- --; and after "having" insert -- , --;

Column 4, line 54, after "and" delete "reused" and insert -- reused --;

Column 5, line 8, after "shown)" insert -- , --;

UNITED STATES PATENT AND TRADEMARK OFFICE
CERTIFICATE OF CORRECTION

PATENT NO. : 5,826,582
DATED : October 27, 1998
INVENTOR(S) : M. Brown

It is certified that error appears in the above-indentified patent and that said Letters Patent is hereby corrected as shown below:

Column 5, lines 10-11, after "provide an" delete "air-tight" and insert --airtight--;

Column 5, lines 39-41, after "shape that" insert --,--; after "one hand" insert --,--; after "37A, and" insert --,--; and after "other hand" insert --,--;

Column 5, line 55, after "double" insert -- -- --;

Column 6, line 5, after "an" delete "air-tight" and insert -- airtight --;

Column 6, line 9, after "an" delete "air-tight" and insert -- airtight --;

Column 6, line 14, after "double" insert -- -- --;

UNITED STATES PATENT AND TRADEMARK OFFICE
CERTIFICATE OF CORRECTION

PATENT NO. : 5,826,582
DATED : October 27, 1998
INVENTOR(S) : M. Brown

It is certified that error appears in the above-indentified patent and that said Letters Patent is hereby corrected as shown below:

Column 6, line 18, after "fiber" insert -- -- --;

Column 6, line 19, after "silicone" insert -- -- --;

Column 6, line 43, after "etc." insert -- , --;

Column 6, lines 59-60, after "for the" delete "manufacture" and insert -- manufacturer --;

Column 6, line 67, after "resilent" delete "open-celled foam," and insert --opened-cell foam,--;

Column 7, lines 2-3, after "by the" delete "open" and insert -- opened – --;

Column 7, lines 4-5, after "The" delete "open" and insert -- opened – --;

Column 7, line 43, after "double" insert -- -- --;

Column 7, line 57 after "respectively" insert --,--;

UNITED STATES PATENT AND TRADEMARK OFFICE
CERTIFICATE OF CORRECTION

PATENT NO. : 5,826,582
DATED : October 27, 1998
INVENTOR(S) : M. Brown

It is certified that error appears in the above-indentified patent and that said Letters Patent is hereby corrected as shown below:

Column 8, lines 2-3, after "die" insert -- -- --;

Column 8, line 3, after "economical" delete "that" and insert --than--;

Column 8, line 19, after "die" insert -- -- --;

Column 8, line 49, after "example," delete "the models" and insert -- two models are the --;

Column 8, line 52, after "emission" insert -- -- --

Column 9, line 61, after "double" insert -- -- --;

Column 10, line 20, after "an" delete "open-celled" and insert -- opened–cell --;

UNITED STATES PATENT AND TRADEMARK OFFICE
CERTIFICATE OF CORRECTION

PATENT NO. : 5,826,582                                    Page 5 of 5
DATED      : October 27, 1998
INVENTOR(S) : M. Brown It is certified that error appears in the above-indentified patent and that said Letters Patent is hereby corrected as shown below:

Column 10, line 39, after "including a" delete "re-usable" and insert -- reusable--;

Column 10, line 46, after "securing the" delete "re-usable" and insert --reusable --;

Abstract, line 10, before "body" delete "re-usable" and insert -- reusable --;

Abstract, line 14, after "die" insert -- – --;

Signed and Sealed this

Seventeenth Day of April, 2001

Attest:

NICHOLAS P. GODICI

Attesting Officer        Acting Director of the United States Patent and Trademark Office